(12) United States Patent
Morelli et al.

(10) Patent No.: US 9,067,078 B2
(45) Date of Patent: Jun. 30, 2015

(54) HERMETIC SEALING METHOD FOR A BATTERY FILLPORT USING SEALING MEMBER

(75) Inventors: Doug Morelli, Forest Lake, MN (US); Bernard Frank Heller, Jr., Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 948 days.

(21) Appl. No.: 12/474,825

(22) Filed: May 29, 2009

(65) Prior Publication Data
US 2010/0304212 A1    Dec. 2, 2010

(51) Int. Cl.
*H01M 2/08*  (2006.01)
*H01M 2/00*  (2006.01)
*A61N 1/378* (2006.01)
*A61N 1/375* (2006.01)

(52) U.S. Cl.
CPC ............. *A61N 1/378* (2013.01); *Y10T 29/4911* (2015.01); *A61N 1/375* (2013.01)

(58) Field of Classification Search
USPC ......................................................... 429/80
See application file for complete search history.

(56) References Cited

U.S. PATENT DOCUMENTS

| | | |
|---|---|---|
| 5,776,632 A | 7/1998 | Honegger |
| 6,117,195 A | 9/2000 | Honegger |
| 6,361,898 B1 * | 3/2002 | Honegger ................. 429/185 |
| 6,844,106 B2 * | 1/2005 | Heller, Jr. ................. 429/80 |
| 7,442,466 B2 | 10/2008 | Casby et al. |
| 2006/0178708 A1 * | 8/2006 | Rorvick et al. ............. 607/36 |
| 2007/0179552 A1 | 8/2007 | Dennis et al. |
| 2007/0247786 A1 | 10/2007 | Aamondt et al. |

FOREIGN PATENT DOCUMENTS

WO    WO 2007/090136    8/2007

OTHER PUBLICATIONS (PCT/US2010/036113) PCT Notification of Transmittal of the International Search Report and the Written Opinion of the International Searching Authority.

* cited by examiner

*Primary Examiner* — Ula C Ruddock
*Assistant Examiner* — Daniel Gatewood

(57) ABSTRACT

A method of manufacturing an energy storage device for a medical device that includes creating an aperture in a case. The aperture includes an inner surface. The method also includes introducing an electrolyte into the case through the aperture and moving a sealing member into the aperture. The sealing member includes an outer surface. Furthermore, the method includes sealing the aperture only with the sealing member and creating a substantially hermetic seal between the inner surface of the aperture and the outer surface of the sealing member.

29 Claims, 4 Drawing Sheets

HERMETIC SEALING METHOD FOR A BATTERY FILLPORT USING SEALING MEMBER

FIELD

The present disclosure relates to an energy storage device for a medical device, and in particular, a method for hermetically sealing a filler aperture in an energy storage device for a medical device.

INTRODUCTION

Several medical devices include an internal energy storage device, such as a battery or a capacitor. The energy storage device supplies power for maintaining proper function. For instance, implantable cardiac pacemaker and defibrillator devices often include batteries, which provide power so that the device can provide predetermined electrical signals to cardiac tissue. These batteries are typically designed to be robust and to have a relatively long operating life.

Oftentimes, manufacture of these batteries includes providing an anode and a cathode into the battery housing. Then, an electrolyte is introduced into the battery housing through a prepared fill port. Subsequently, the fill port is sealed.

Batteries and methods for sealing the fill port can include a number of separate components and/or can require several steps for creating and sealing the port. Accordingly, manufacturing costs can be relatively high. Also, sealing the fill port can be relatively complex.

SUMMARY

This section provides a general summary of the disclosure, and is not a comprehensive disclosure of its full scope or all of its features.

A method of manufacturing an energy storage device for a medical device is disclosed that includes creating an aperture in a case. The aperture includes an inner surface. The method also includes introducing an electrolyte into the case through the aperture and moving a sealing member into the aperture. The sealing member includes an outer surface. Furthermore, the method includes sealing the aperture only with the sealing member and creating a substantially hermetic seal between the inner surface of the aperture and the outer surface of the sealing member.

Also, an energy storage device for a medical device is disclosed that includes a cell assembly and a case that houses the cell assembly. The case includes an aperture for introducing an electrolyte into the case, and the aperture includes an inner surface. Moreover, the device includes a sealing member with an outer surface that is frictionally fit within the aperture. A substantially hermetic seal is formed between the sealing member and the case only by the frictional fit between the outer surface of the sealing member and the inner surface of the aperture.

Still further, a method of manufacturing a battery for a medical device is disclosed. The method includes creating a through-hole in a battery case having a substantially constant diameter. The method also includes filleting an outer rim of the through-hole and chamfering an inner rim of the through-hole. The method further includes introducing an electrolyte into the battery case through the through-hole. Also, the method includes providing a substantially spherical sealing member having a hardness that is greater than the battery case adjacent the through-hole. In addition, the method includes sealing the through-hole only with the spherical sealing member only by moving the spherical sealing member into the through-hole to deform the battery case and to create a substantially hermetic and continuous line seal between an inner surface of the through-hole and an outer surface of the spherical sealing member, leaving the spherical sealing member disposed entirely between the inner and outer rims of the through-hole.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Exemplary embodiments will now be described more fully with reference to the accompanying drawings.

Figure 1:
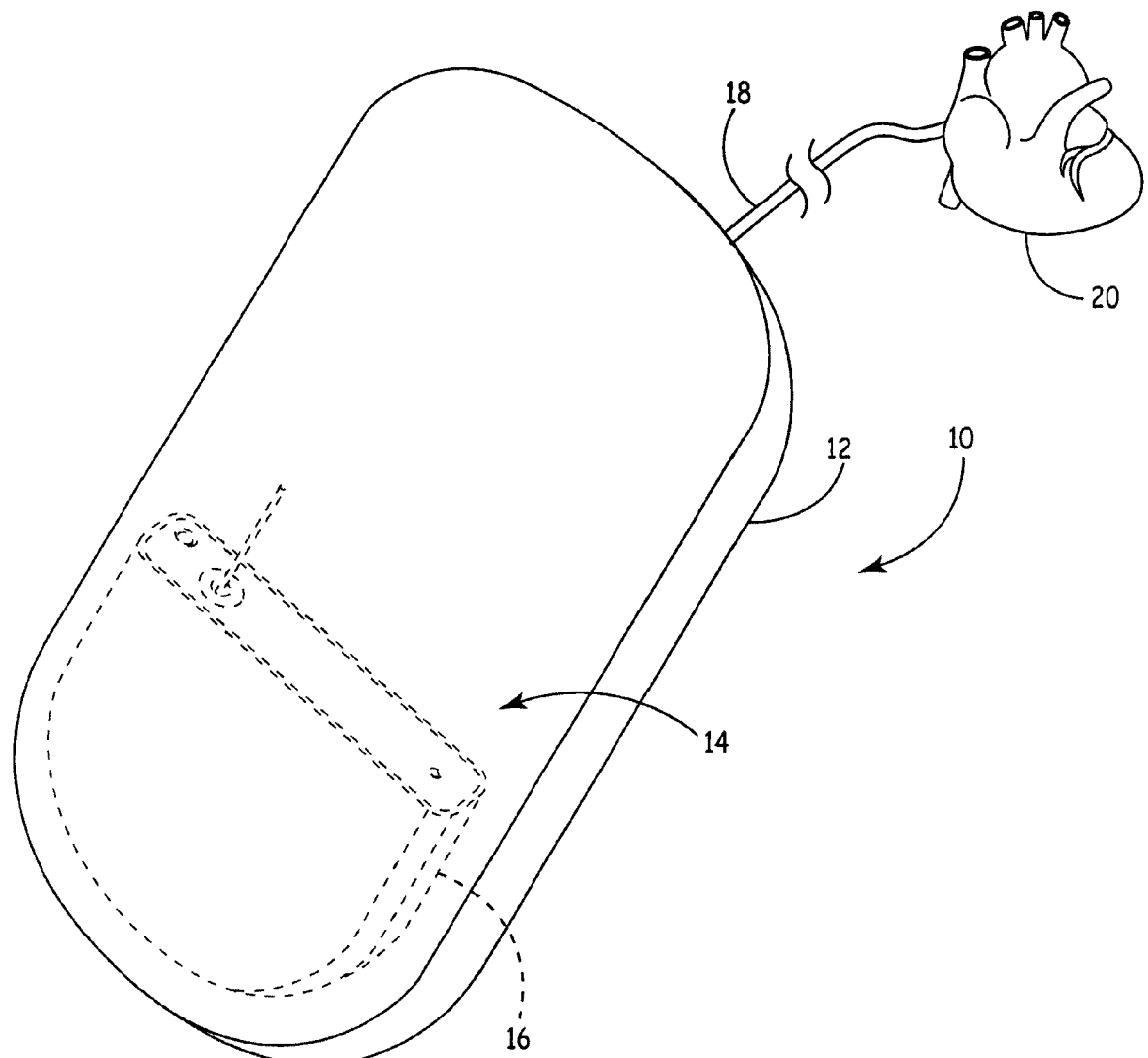
FIG. 1 is a schematic view of a medical device having a battery according to various embodiments of the present disclosure.

Referring initially to FIG. 1, a medical device 10 is schematically illustrated. The medical device 10 can include a housing assembly 12 and various internal components, generally indicated at 14. The internal components 14 can be housed within the housing assembly 12. The internal components 14 can include a computerized controller, logic, and circuitry (not specifically shown) for operation of the medical device 10. The internal components 14 can also include an energy storage device, such as a battery 16 (shown in phantom in FIG. 1). As will be discussed, the battery 16 stores and supplies power to other internal components 14 of the medical device 10.

It will be appreciated that the medical device 10 can be of any suitable type. For instance, the medical device 10 can be an implantable cardiac pacemaker (IPG) or a defibrillator (ICD). As such, the medical device 10 can include a flexible lead 18 that extends from the housing assembly 12 and that electrically connects the internal components 14 of the medical device 10 to cardiac tissue 20 of a patient. Thus, the internal components 14 of the medical device 10 can generate electrical signals that are transmitted to the cardiac tissue 20 via the lead 18 to maintain proper function of the cardiac tissue 20.

It will also be appreciated that the medical device 10 can include any suitable energy storage device or electrochemical cell other than a battery 16. For instance, the medical device 10 can include a capacitor for supplying stored energy thereto.

Figure 2:
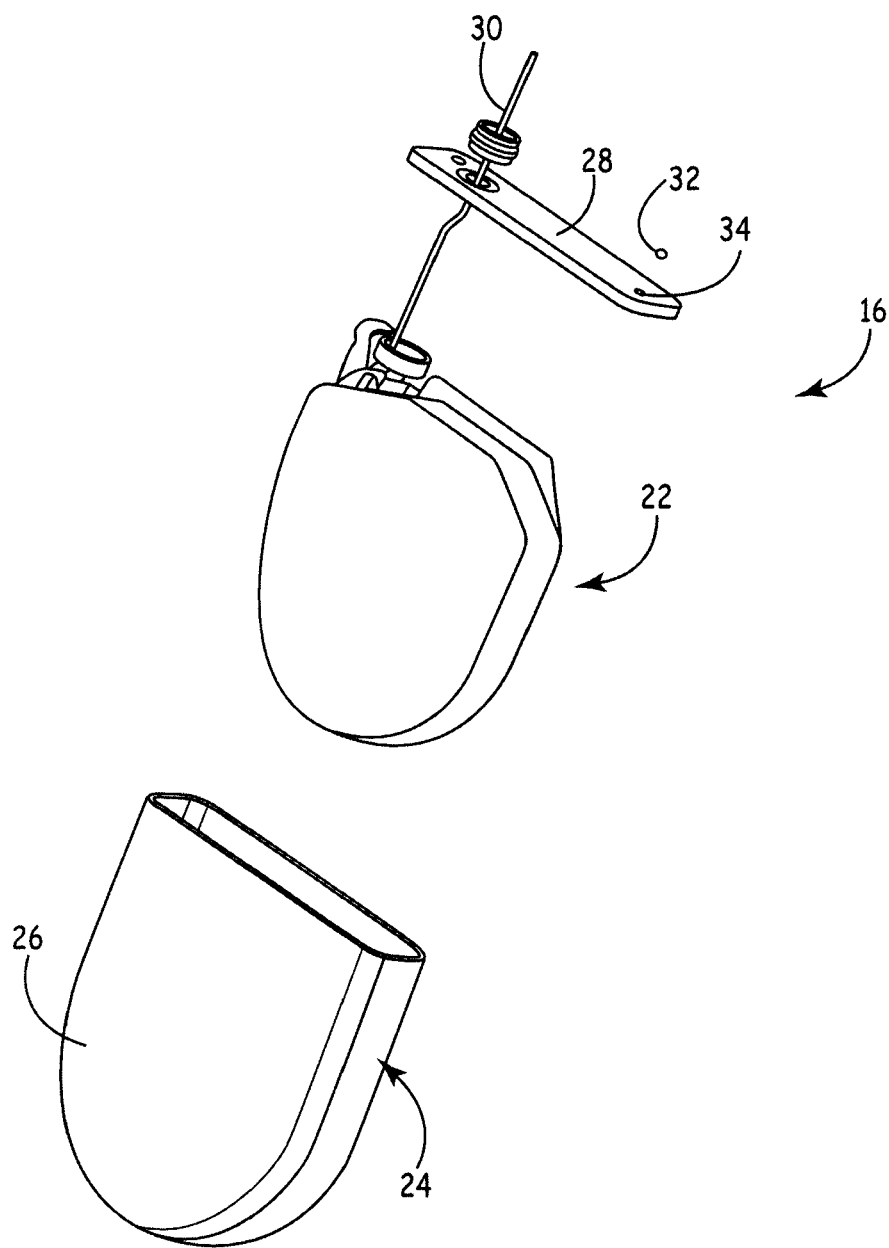
FIG. 2 is an exploded view of the battery of the medical device of FIG. 1.

Referring now to FIG. 2, an exemplary embodiment of the battery 16 of the medical device 10 is shown in greater detail. The battery 16 can include a cell assembly 22. The cell assembly 22 can include an anode, cathode, separator, and an electrolyte (not specifically shown). A chemical reaction between the cathode and the anode can generate electricity for the medical device 10.

The battery 16 can also include a battery case 24 that encases the cell assembly 22. The battery case 24 can include a main portion 26 and a header portion 28. The main portion 26 can be relatively thin-walled and hollow and can receive the cell assembly 22. The header portion 28 can be a thin, elongate plate that is fixed to the main portion 26 to encapsulate the cell assembly 22 within the battery case 24. The main portion 26 and the header portion 28 can be fixed in any suitable fashion. For instance, the header portion 28 can be welded to the main portion 26 about an entire periphery of the header portion 28 in some embodiments.

The battery 16 can also include a connector 30 that extends through the header portion 28. The connector 30 can be an electrically conductive wire or pin that is electrically connected to the cell assembly 22 and that is electrically insulated from the header portion 28. It will be appreciated that the connector 30 can be electrically coupled to the internal components 14 of the medical device 10 for supplying electricity from the cell assembly 22 thereto.

Figure 5:
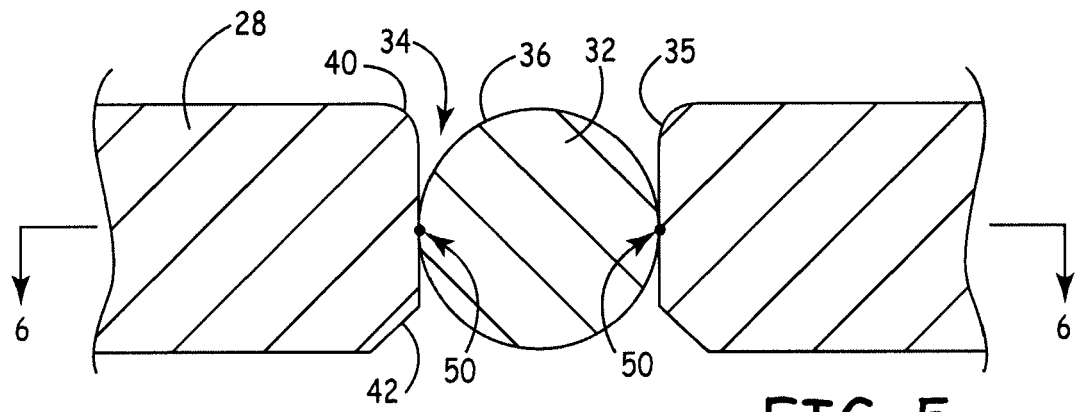
FIG. 5 is a side view of a header portion of the battery of FIG. 2, which includes a filler aperture, the filler aperture shown in a sealed state.

As shown in FIGS. 2 and 5, the battery 16 can include a sealing member 32 that seals a filler aperture 34 included in the header portion 28. As will be discussed in greater detail, the filler aperture 34 can be used for introducing an electrolyte into the battery case 24, and the sealing member 32 can seal the filler aperture 34 so that the electrolyte is unlikely to leak from the battery case 24 and/or so that foreign materials are unlikely to enter the battery case 24 and contaminate the cell assembly 22.

More specifically, the filler aperture 34 can be a through hole with an inner surface 35 that extends through a thickness of the header portion 28. Additionally, the sealing member 32 can be substantially spherical and can have an outer surface 36.

As will be discussed in greater detail below, the sealing member 32 can be frictionally fit within the filler aperture 34 to seal the filler aperture 34. More specifically, as shown in FIG. 5, the sealing member 32 can be frictionally fit into the filler aperture 34 so that a substantially hermetic seal is formed between the sealing member 32 and the battery case 24 only by the frictional fit between the outer surface 36 of the sealing member 32 and the inner surface 35 of the filler aperture 34.

Accordingly, as will be discussed in greater detail below, the sealing member 32 can significantly facilitate hermetic sealing of the filler aperture 34 such that the hermeticity of the battery case 24 is unlikely to be compromised. Moreover, the battery 16 can be less expensive to manufacture because relatively few parts are needed to seal the filler aperture 34.

Figure 3:
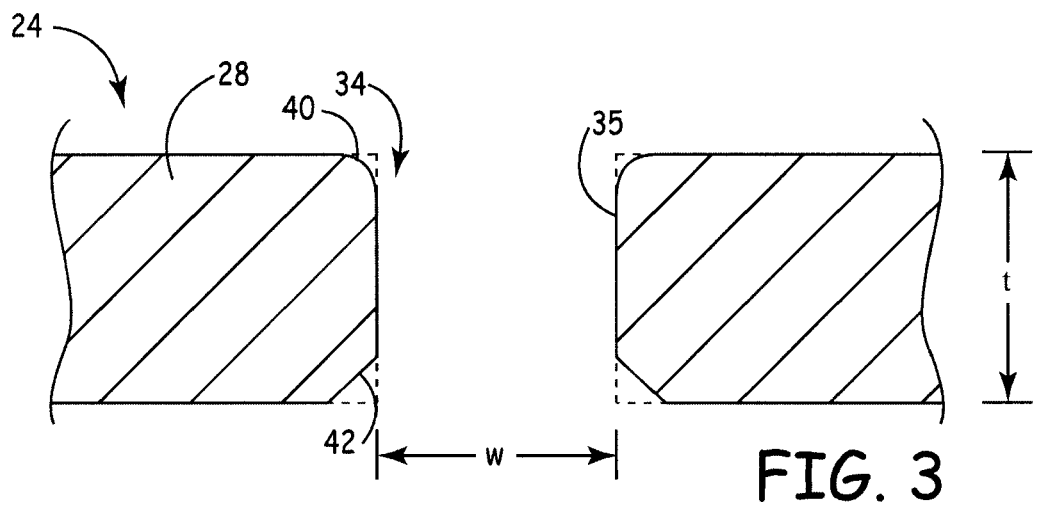
FIG. 3 is a side view of a header portion of the battery of FIG. 2, which includes a filler aperture, the filler aperture shown in an unsealed state.
Figure 4:
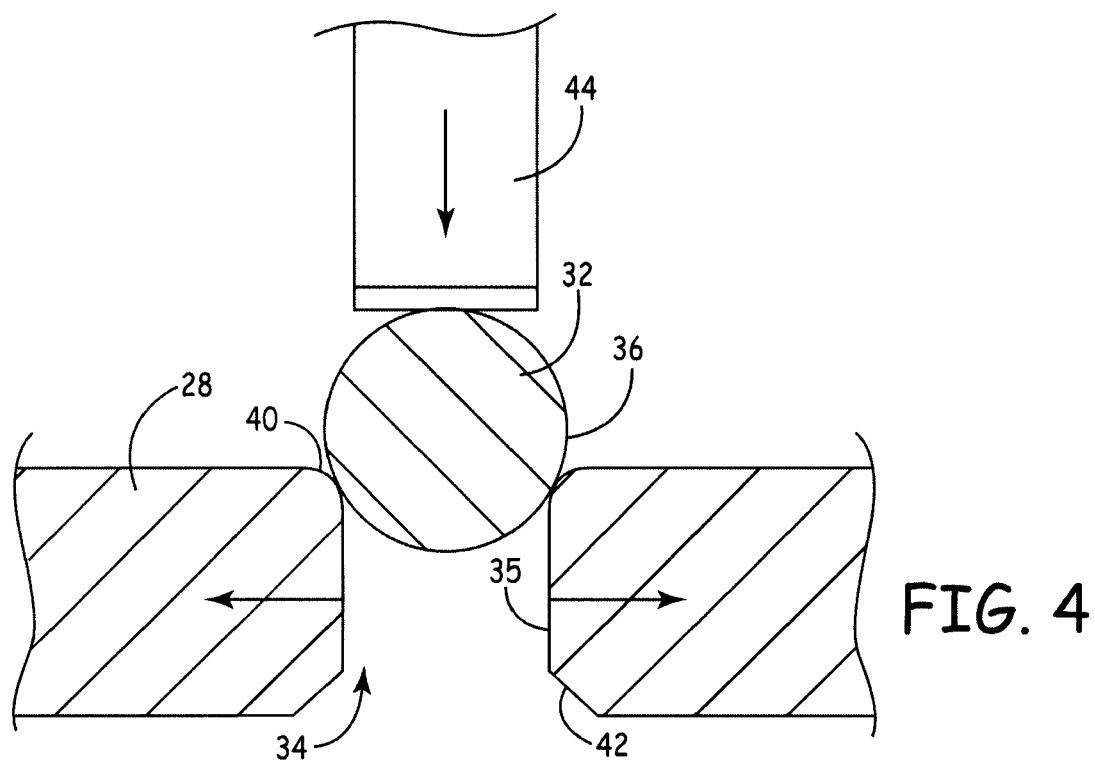
FIG. 4 is a schematic view of a method of sealing the filler aperture of the battery of FIG. 2 according to various embodiments of the present disclosure.

Referring now to FIGS. 3-5, an exemplary embodiment of a method of manufacturing the battery 16 and sealing the filler aperture 34 will be discussed. As shown in FIG. 3, the manufacturing method can include creating the filler aperture 34 in the battery case 24. The filler aperture 34 can be created in any suitable location in the battery case 24 including the header portion 28. Also, the filler aperture 34 can be formed in the header portion 28 before the header portion 28 is fixed to the main portion 26 of the battery case 24.

The filler aperture 34 can be created in any suitable fashion, such as drilling (laser drilling or otherwise), punching, and the like. Also, the filler aperture 34 can be of any suitable shape and size. For instance, the filler aperture 34 can have a substantially constant width, w, (e.g., a diameter) of approximately 0.026 inches to 0.030 inches, where the thickness, t, of the header portion 28 is approximately 0.030 inches to 0.034 inches adjacent the aperture 34.

When initially formed, the width, w, of the filler aperture 34 can be substantially constant along the entire thickness, t, of the header portion 28. Then, an outer rim 40 of the filler aperture 34 can be filleted as represented by phantom lines in FIG. 3. The outer rim 40 can be filleted at any suitable radius, such as approximately 0.008 inches. Also, an inner rim 42 of the filler aperture 34 can be chamfered as represented by phantom lines in FIG. 3. The inner rim 42 of the filler aperture 34 can chamfered to any suitable orientation and/or dimension, such as a chamfer of approximately 45° by 0.005 inches, maximum. It will be appreciated that the inner rim 42 could be filleted and the outer rim 40 could be chamfered in some embodiments. It will also be appreciated that the outer and inner rim 40, 42 could both be chamfered or could both be filleted without departing from the scope of the present disclosure. Furthermore, it will be appreciated that the filler aperture 34 can retain a substantially constant width, w, between the outer and inner rim 40, 42 such that the narrowest portion of the filler aperture 34 is located between the outer and inner rim 40, 42. As will be discussed, the sealing member 32 can be more easily centered with respect to the filler aperture 34 because the outer rim 40 is filleted. Also, because the inner rim 42 is chamfered, the inner rim 42 is unlikely to include burrs or any other unwanted materials that might otherwise interfere with surrounding structures, such as the cell assembly 22 (FIG. 2).

Once the cell assembly 22 is disposed in the main portion 26 of the battery case 24 and the header portion 28 has been joined to the main portion 26, the electrolyte can be supplied into the battery case 24 through the filler aperture 34. The electrolyte can be of any suitable type.

Next, as shown in FIG. 4, the sealing member 32 can be provided for sealing the filler aperture 34. The sealing member 32 can be of any suitable size and shape. For instance, the sealing member 32 can be spherical and can have a diameter of approximately 0.03125 inches. As mentioned above, the filleted outer rim 40 can help center the sealing member 32 with respect to the filler aperture 34.

Then, as shown in FIG. 4, the sealing member 32 can be moved into the filler aperture 34. The sealing member 32 can be moved into the filler aperture 34 in any suitable fashion. For instance, in some embodiments, a press tool 44 can be used to move the sealing member 32 into the filler aperture 34. The press tool 44 can impart a pressing force on the sealing member 32 (represented by a downward vertical arrow in FIG. 4) to move the sealing member 32 generally parallel to the axis of the filler aperture 34 and into the filler aperture 34. The press tool 44 can move the sealing member 32 into the filler aperture 34 in any suitable fashion to ensure that the sealing member 32 properly seats inside the filler aperture 34. For instance, the press tool 44 can move at a speed of approximately 0.5 inches/second and impart a load of approximately 150 pounds to 185 pounds onto the sealing member 32.

In some embodiments, the movement of the sealing member 32 into the filler aperture 34 causes the header portion 28 to deform. For instance, the header portion 28 can elastically and/or plastically deform such that the width, w, of the filler aperture 34 expands as represented by two horizontal arrows in FIG. 4. In some embodiments, the sealing member 32 can have a greater material hardness than that of the header portion 28 to ensure that the header portion 28 deforms as the sealing member 32 moves into the filler aperture 34. More specifically, the sealing member 32 can be made from or can include grade 5 titanium, whereas the header portion 28 (at least adjacent the filler aperture 34) can be made from or can include grade 1 or grade 2 titanium to ensure that the sealing member 32 has a greater hardness.

The sealing member 32 can be moved to any suitable depth within the filler aperture 34. For instance, as shown in FIG. 5, the sealing member 32 can be moved such that the outer surface 36 of the sealing member 32 is disposed entirely between the outer rim 40 and the inner rim 42 of the filler aperture 34. Accordingly, the sealing member 32 is unlikely to interfere with surrounding structure on either side of the header portion 28. It will be appreciated, however, that the sealing member 32 can protrude slightly from the outer rim 40 and/or the inner rim 42 without departing from the scope of the present disclosure.

Figure 6:
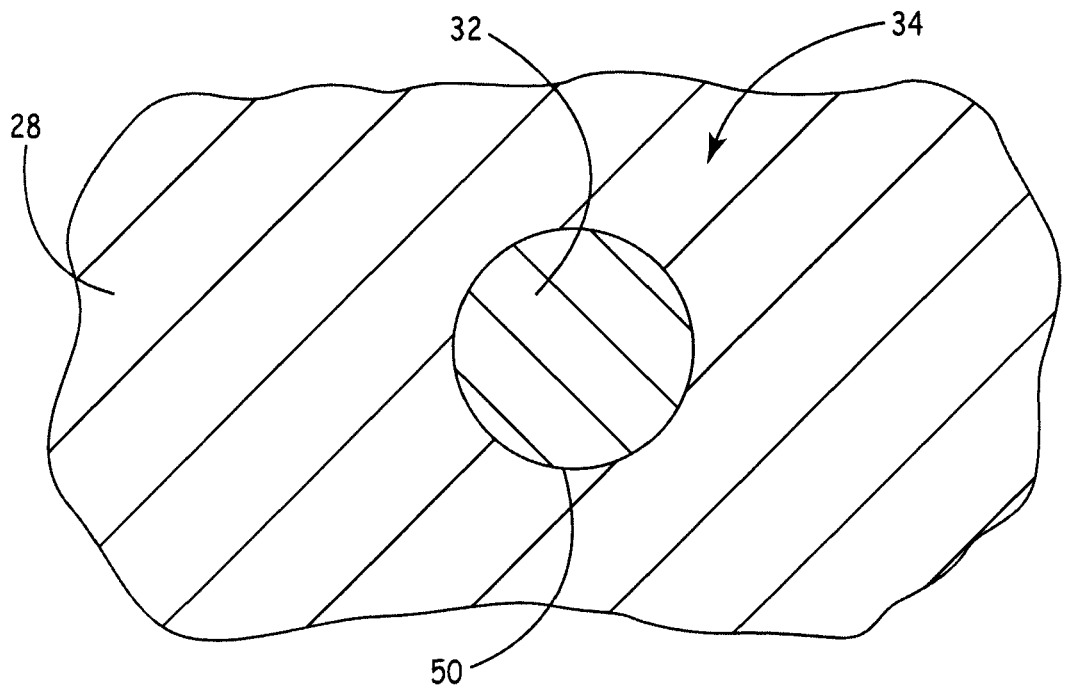
FIG. 6 is a sectional view of the header portion of the battery taken along line 6-6 of FIG. 5.

Thus, by moving the sealing member 32 into the filler aperture 34, the outer surface 36 of the sealing member 32 can seal against the inner surface 35 of the filler aperture 34. More specifically, a continuous, circular line seal 50 in the shape of a closed loop can be created between the sealing member 32 and the inner surface 35 (FIGS. 5 and 6) due to movement of the sealing member 32 into the filler aperture 34. It will be appreciated that the line seal 50 can provide the only seal of the filler aperture 34, and yet the line seal 50 can provide a robust seal of the filler aperture 34. For instance, the line seal 50 can have a leak rate less than approximately $1.0 \times 10^{-7}$ std ccHe/sec.

Accordingly, the filler aperture 34 can be sealed in an uncomplicated manner with relatively few parts. Accordingly, part costs for the battery 16 can be reduced, and manufacturing time and effort can be significantly reduced as well. Moreover, the sealing member 32 can be relatively compact, making the battery 16 more compact and/or allowing surrounding structure to be bigger. For instance, the anode and cathode of the cell assembly 22 can be larger, thereby advantageously increasing the energy density of the battery 16.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

Exemplary embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A method of manufacturing an energy storage device for a medical device comprising:
   creating an aperture in a case, the aperture including an inner surface;
   introducing an electrolyte into the case through the aperture; and
   moving a sealing member into the aperture, the sealing member including an outer surface, the sealing member being frictionally fitted within the aperture;
   wherein a substantially hermetic seal is formed between the sealing member and the case only by the frictional fit between the outer surface of the sealing member and the inner surface of the aperture, wherein the sealing member within the aperture is the only sealing member and only component used to seal the aperture.

2. The method of claim 1, further comprising deforming the case with the sealing member when moving the sealing member into the aperture.

3. The method of claim 2, further comprising providing a sealing member with a greater hardness than that of the case so that the case is deformed when moving the sealing member into the aperture.

4. The method of claim 3, wherein the sealing member includes grade 5 titanium and the case includes at least one of grade 1 titanium and grade 2titanium.

5. The method of claim 1, wherein sealing the aperture comprises creating a continuous line seal in the shape of a closed loop about the sealing member between the outer surface of the sealing member and the inner surface of the aperture.

6. The method of claim 1, wherein the sealing member is substantially spherical.

7. The method of claim 1, wherein creating the aperture comprises creating a through-hole through the case.

8. The method of claim 7, further comprising chamfering an outer rim of the through-hole, filleting the outer rim of the through-hole, or both.

9. The method of claim 7, further comprising chamfering an inner rim of the through-hole, filleting the inner rim of the through-hole, or both.

10. The method of claim 7, further comprising forming the through-hole to have a substantially constant width before filleting, chamfering, or both filleting and chamfering a rim of the through-hole.

11. The method of claim 1, wherein sealing the aperture comprises moving the sealing member into the aperture so that the sealing member is disposed entirely between an inner rim and an outer rim of the aperture.

12. The method of claim 1, wherein sealing the aperture comprises creating a seal having a leak rate less than $1.0 \times 10^{-7}$ std ccHe/sec using only the sealing member.

13. The method of claim 1, wherein sealing the aperture comprises moving the sealing member into the aperture at a press force of at least approximately 150 pounds and at most approximately 185 pounds at approximately 0.5 inches per second.

14. An energy storage device for a medical device comprising:
   a cell assembly;
   a case that houses the cell assembly, the case including an aperture for introducing an electrolyte into the case, the aperture including an inner surface; and
   a sealing member with an outer surface that is frictionally fit within the aperture, wherein a substantially hermetic seal is formed between the sealing member and the case only by the frictional fit between the outer surface of the sealing member and the inner surface of the aperture, wherein the sealing member within the aperture is the only sealing member and only component used to seal the aperture.

15. The energy storage device of claim 14, wherein the sealing member has a greater hardness than that of the case.

16. The energy storage device of claim 15, wherein the sealing member includes grade 5 titanium and the case includes at least one of grade 1 titanium and grade 2 titanium.

17. The energy storage device of claim 14, wherein the hermetic seal defines a continuous line seal in the shape of a closed loop about the sealing member between the outer surface of the sealing member and the inner surface of the aperture.

18. The energy storage device of claim 14, wherein the sealing member is substantially spherical.

19. The energy storage device of claim 14, wherein the case includes a header and the aperture extends through the header of the case.

20. The energy storage device of claim 14, wherein the aperture has a filleted rim.

21. The energy storage device of claim 14, wherein the aperture has a chamfered rim.

22. The energy storage device of claim 14, wherein the aperture has an inner rim that is chamfered and an outer rim that is filleted.

23. The energy storage device of claim 14, wherein the aperture includes an inner rim and an outer rim, and wherein a narrowest portion of the aperture is located between the inner and outer rims.

24. The energy storage device of claim 14, wherein the sealing member is disposed entirely between an inner rim and an outer rim of the aperture.

25. The energy storage device of claim 14, wherein the hermetic seal has a leak rate less than approximately $1.0 \times 10^{-7}$ std ccHe/sec using only the sealing member.

26. The energy storage device of claim 14, wherein the aperture has a width of at least approximately 0.026 inches and approximately 0.030 inches.

27. The energy storage device of claim 14, wherein the sealing member is substantially spherical and has a diameter of approximately 0.03125 inches.

28. The energy storage device of claim 14, wherein the case has thickness of at least approximately 0.030 inches and at most approximately 0.034 inches adjacent the aperture.

29. A method of manufacturing a battery for a medical device comprising:
   creating a through-hole in a battery case having a substantially constant diameter;
   filleting an outer rim of the through-hole;
   chamfering an inner rim of the through-hole;
   introducing an electrolyte into the battery case through the through-hole;
   providing a substantially spherical sealing member having a hardness that is greater than the battery case adjacent the through-hole; and
   moving the spherical sealing member into the through-hole to deform the battery case, the sealing member being frictionally fitted within the through-hole wherein a substantially hermetic seal is formed between the sealing member and the case only by the frictional fit between the outer surface of the sealing member and the inner surface of the through-hole, wherein the sealing member within the through-hole is the only sealing member and only component used to seal the through-hole.

* * * * *

UNITED STATES PATENT AND TRADEMARK OFFICE
CERTIFICATE OF CORRECTION

PATENT NO. : 9,067,078 B2  
APPLICATION NO. : 12/474825  
DATED : June 30, 2015  
INVENTOR(S) : Morelli et al.

Page 1 of 1

It is certified that error appears in the above-identified patent and that said Letters Patent is hereby corrected as shown below:

In the Claims

Claim 4; Column 7; Line 12, delete "...at least one of grade 1 titanium and grade 2titanium..." and insert in place thereof -- at least one of grade 1 titanium and grade 2 titanium --.

Signed and Sealed this  
Twenty-sixth Day of April, 2016

Michelle K. Lee  
*Director of the United States Patent and Trademark Office*